(12) United States Patent
Ishida et al.

(10) Patent No.: US 9,704,294 B2
(45) Date of Patent: Jul. 11, 2017

(54) IMAGE PROCESSING APPARATUS AND IMAGE PROCESSING METHOD

(71) Applicant: CANON KABUSHIKI KAISHA, Tokyo (JP)

(72) Inventors: Takuya Ishida, Tokyo (JP); Kiyohide Satoh, Kawasaki (JP); Ryo Ishikawa, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 72 days.

(21) Appl. No.: 14/610,190

(22) Filed: Jan. 30, 2015

(65) Prior Publication Data

US 2015/0235369 A1 Aug. 20, 2015

(30) Foreign Application Priority Data

Feb. 14, 2014 (JP) ................. 2014-026899

(51) Int. Cl.
*A61B 6/00* (2006.01)
*A61B 5/00* (2006.01)
*G06T 7/00* (2017.01)
*G06T 19/00* (2011.01)
*G06T 15/08* (2011.01)

(52) U.S. Cl.
CPC ............ *G06T 19/00* (2013.01); *A61B 5/0033* (2013.01); *G06T 15/08* (2013.01); *A61B 6/5223* (2013.01); *G06T 2207/10072* (2013.01); *G06T 2219/008* (2013.01)

(58) Field of Classification Search
None
See application file for complete search history.

(56) References Cited

U.S. PATENT DOCUMENTS

| | | | |
|---|---|---|---|
| 2008/0025587 A1* | 1/2008 | Asbeck | G06T 7/606 382/128 |
| 2009/0063118 A1* | 3/2009 | Dachille | G06F 17/30262 703/11 |
| 2009/0162813 A1* | 6/2009 | Glor | A61C 1/084 433/196 |
| 2011/0091086 A1* | 4/2011 | Seko | A61B 8/463 382/131 |
| 2012/0093278 A1* | 4/2012 | Tsukagoshi | G06T 11/008 378/4 |

FOREIGN PATENT DOCUMENTS

| | | |
|---|---|---|
| JP | 2010-000133 A | 1/2010 |
| JP | 2010-227215 A | 10/2010 |

\* cited by examiner

*Primary Examiner* — Utpal Shah
(74) *Attorney, Agent, or Firm* — Carter, DeLuca, Farrell & Schmidt, LLP

(57) ABSTRACT

A curved slice is obtained from a three-dimensional tomographic image of an object based on a reference position in the three-dimensional tomographic image. A two-dimensional tomographic image corresponding to the curved slice is generated from the three-dimensional tomographic image.

17 Claims, 8 Drawing Sheets

F I G. 6
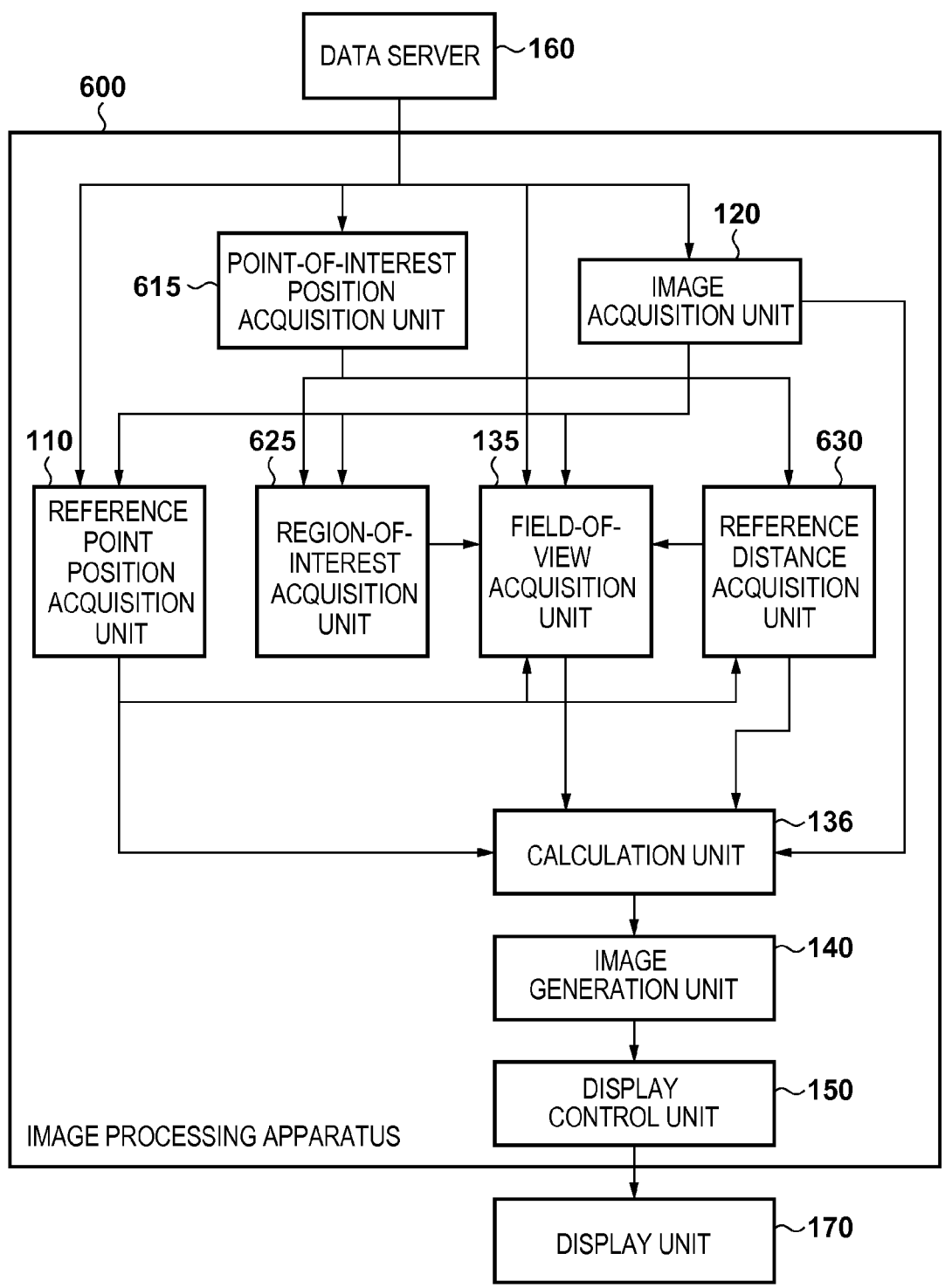

IMAGE PROCESSING APPARATUS AND IMAGE PROCESSING METHOD

BACKGROUND OF THE INVENTION

Field of the Invention

The present invention relates to a technique for presenting a three-dimensional tomographic image.

Description of the Related Art

In the medical field, a doctor makes a diagnosis by using three-dimensional tomographic images (three-dimensional image data representing three-dimensional information inside an object) captured by a plurality of modalities or in a plurality of modes, three-dimensional tomographic images captured on different times, or three-dimensional tomographic images captured in different body postures. In order to use a plurality of types of three-dimensional tomographic images for a diagnosis, it is important to observe the same region of an object in the respective three-dimensional tomographic images. It is especially important to associate (identify) a region (a region of interest or a lesion area of interest) such as a lesion area of interest between images. While seeing the image of a lesion area of interest pointed out on one three-dimensional tomographic image, the doctor searches another three-dimensional tomographic image for a region (a corresponding region or a corresponding lesion area) corresponding to the lesion area by using, as clues, similarities in the shape of the lesion area, the appearance of a neighboring portion of the lesion area, and the like. Even in a field other than the medical field, in order to inspect the internal state of an object, three-dimensional tomographic images of the object are captured by a plurality of apparatuses, and another image is searched for a point of interest detected in one image.

Japanese Patent Laid-Open No. 2010-227215 discloses a technique of estimating a deformation between three-dimensional tomographic images captured in different body postures. According to this technique, identical slices of images having undergone deformation alignment are synchronously displayed and can be compared.

Japanese Patent Laid-Open No. 2010-133 discloses a technique of performing normalization processing of a breast region based on a papilla and displaying support information for search in a comparison region, in order to compare a region of interest between one image and the other image in captured left and right breast images.

However, the method disclosed in Japanese Patent Laid-Open No. 2010-227215 still has a problem that it is difficult to accurately perform deformation alignment. Since slices do not always coincide with each other owing to an alignment error or the like, the comparison sometimes becomes difficult depending on the degree of error. The method disclosed in Japanese Patent Laid-Open No. 2010-133 has a problem that auxiliary information in a three-dimensional space cannot be presented because the target image is a two-dimensional image.

SUMMARY OF THE INVENTION

The present invention has been made in consideration of the above problems, and provides a technique capable of generating a tomogram desirable for comparison and search regardless of the deformation of an object.

According to the first aspect of the present invention, there is provided an image processing apparatus comprising: a calculation unit configured to obtain a curved slice from a three-dimensional tomographic image of an object based on a reference position in the three-dimensional tomographic image; and a generation unit configured to generate a two-dimensional tomographic image corresponding to the curved slice from the three-dimensional tomographic image.

According to the second aspect of the present invention, there is provided an image processing method to be performed by an image processing apparatus, comprising: a calculation step of obtaining a curved slice from a three-dimensional tomographic image of an object based on a reference position in the three-dimensional tomographic image; and a generation step of generating a two-dimensional tomographic image corresponding to the curved slice from the three-dimensional tomographic image.

Further features of the present invention will become apparent from the following description of exemplary embodiments (with reference to the attached drawings).

BRIEF DESCRIPTION OF THE DRAWINGS

FIG. 6 is a block diagram showing an example of the configuration of a system;

DESCRIPTION OF THE EMBODIMENTS

Embodiments of the present invention will now be described with reference to the accompanying drawings. Note that each embodiment to be described below will exemplify a case where the present invention is specifically carried out, and is a specific embodiment of an arrangement described in the scope of claims.

[First Embodiment]

The first embodiment will explain a system that presents, to an operator, the image of a slice obtained by clipping an object (strictly, an object image represented by a three-dimensional tomographic image) on a spherical surface centered on a reference point in a three-dimensional tomographic image (three-dimensional volume image) and having a designated distance as the radius. This system assumes a case where an object has a structural property in which even if the object is deformed, the distance from the reference point of the object to each point in the object does not greatly change. This system has a feature that the image of a slice in which a predetermined region (for example, a lesion area) in an object is highly likely to exist can be reproducibly presented by using the above-mentioned property of the object. The vicinity of the same region of the object can be easily observed in respective three-dimensional tomographic images by designating the same distance regardless of the difference in the date & time, body posture, or apparatus for capturing the three-dimensional tomographic image of an object. This embodiment will explain a case where the object is a breast and the reference point (reference point position) is a papilla (papilla position). This is because the breast has a structural property in which even if the object is deformed, the distance from the papilla position to each point in the breast does not greatly change.

Figure 1:
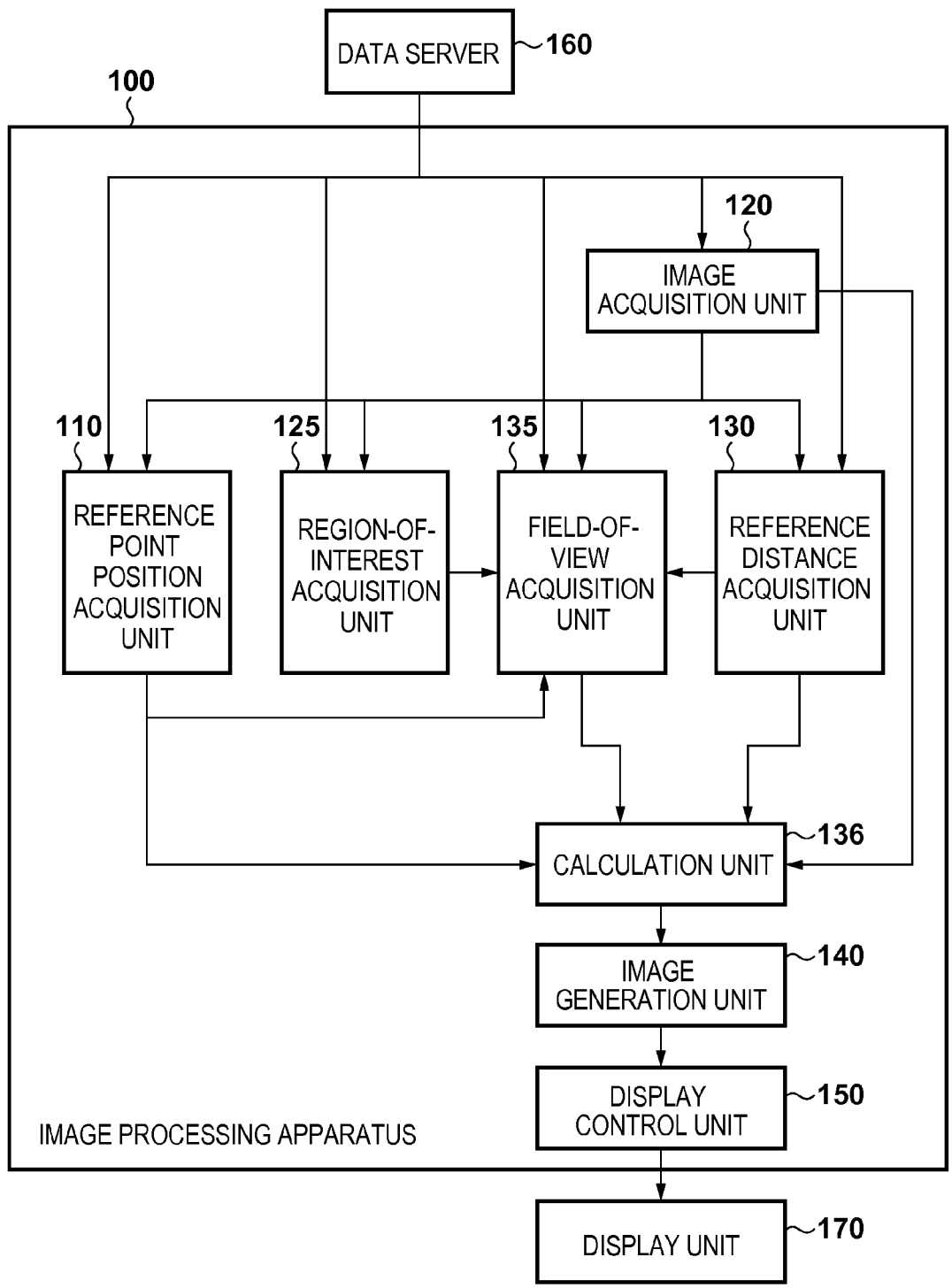
FIG. 1 is a block diagram showing an example of the configuration of a system.

An example of the configuration of the system according to this embodiment will be described first with reference to the block diagram of FIG. 1. As shown in FIG. 1, the system according to this embodiment includes a data server 160, an image processing apparatus 100, and a display unit 170.

The data server 160 will be described first. A three-dimensional tomographic image of an object, and information that defines the region of the object in the three-dimensional tomographic image are registered in the data server 160. The data server 160 properly sends these pieces of registered information to the image processing apparatus 100 in accordance with a request from the image processing apparatus 100. Although the data server 160 is illustrated as an apparatus separate from the image processing apparatus 100 in FIG. 1, it is not limited to this and may be assembled in the image processing apparatus 100. For example, information described as one registered in the data server 160 may be registered in advance in the internal memory of the image processing apparatus 100.

The display unit 170 will be described next. The display unit 170 is constituted by a CRT, a liquid crystal screen, or the like. The display unit 170 can display images and characters output from the image processing apparatus 100.

The image processing apparatus 100 will be described next. An image acquisition unit 120 acquires information that defines, from the data server 160, a three-dimensional tomographic image of an object and the region (object region) of the object in the three-dimensional tomographic image.

A reference point position acquisition unit 110 acquires, as the position (reference point position) of a reference point, the position of a papilla in the three-dimensional tomographic image acquired by the image acquisition unit 120. A region-of-interest acquisition unit 125 acquires information that defines a region of interest in the three-dimensional tomographic image acquired by the image acquisition unit 120. A reference distance acquisition unit 130 acquires and sets a reference distance from the reference point position. A field-of-view acquisition unit 135 acquires the field of view of a two-dimensional tomographic image to be finally generated.

A calculation unit 136 obtains a curved slice in a three-dimensional tomographic image by using the reference point position, the reference distance, and the field of view. An image generation unit 140 generates a two-dimensional tomographic image on the curved slice. For example, the calculation unit 136 obtains a spherical surface centered on the reference point and having the reference distance as the radius, and calculates, based on the field of view, a partial region that is clipped as a curved slice on the spherical surface. The image generation unit 140 generates, from the three-dimensional tomographic image, a two-dimensional tomographic image (to be referred to as a spherical tomogram hereinafter) based on the calculated curved slice (to be referred to as a spherical slice hereinafter). The image generation unit 140 outputs the generated spherical tomogram to a display control unit 150.

Needless to say, the image generation unit 140 may output information other than the spherical tomogram to the display control unit 150. For example, the image generation unit 140 may output information (image information or character information) about a patient, information (image information or character information) about an object, information about an imaging device, date & time information, and the like.

The image generation unit 140 may output a spherical tomogram and various kinds of information to a unit other than the display control unit 150. For example, the image generation unit 140 may transmit a spherical tomogram and various other kinds of information to another device connected to this apparatus. The display control unit 150 controls the display unit 170 to display a spherical tomogram and the like output from the image generation unit 140.

Figure 3:
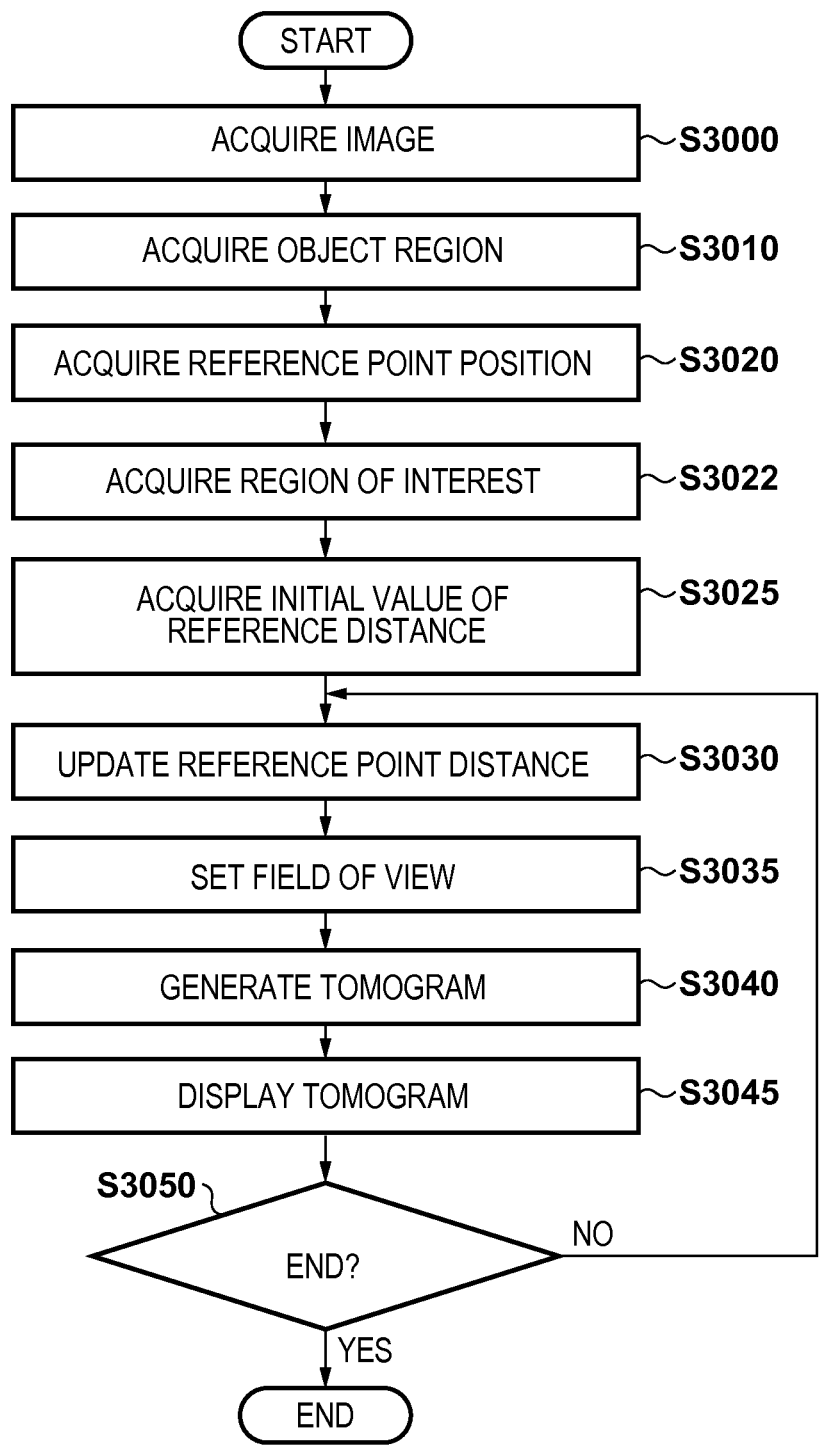
FIG. 3 is a flowchart showing processing to be performed by an image processing apparatus 100.

In FIG. 1, the image processing apparatus 100 includes the image acquisition unit 120, the reference point position acquisition unit 110, the region-of-interest acquisition unit 125, the field-of-view acquisition unit 135, the reference distance acquisition unit 130, the calculation unit 136, the image generation unit 140, and the display control unit 150. However, not all these functional units need be incorporated in the image processing apparatus 100, and one or more of these functional units may be incorporated in a separate apparatus. In this case, this separate apparatus and the image processing apparatus 100 need to be connected so that they can communicate with each other. Next, processing to be performed by the image processing apparatus 100 will be explained with reference to the flowchart of FIG. 3.

(Step S3000: Acquisition of Image)

In step S3000, the image acquisition unit 120 acquires a three-dimensional tomographic image of an object from the data server 160. The "three-dimensional tomographic image" is, for example, an MRI image, a CT image, or an ultrasonic image, and may be an image obtained by any other modality. The "three-dimensional tomographic image" may be a set of three-dimensional tomographic images obtained by imaging an object by a plurality of modalities, in a plurality of imaging modes, on different times, or in different body postures. When the image acquisition unit 120 acquires a plurality of three-dimensional tomographic images, the following processing is performed on each three-dimensional tomographic image. That is, the calculation unit 136 and the image generation unit 140 in the image processing apparatus according to the present invention perform processes on each of the plurality of three-dimensional tomographic images.

(Step S3010: Acquisition of Object Region)

In step S3010, the image acquisition unit 120 acquires, from the data server 160, information that defines an object region (in this embodiment, a region where a breast is captured) in the three-dimensional tomographic image acquired in step S3000. The "information" to be acquired is, for example, a three-dimensional label image in which different values are added to an object region and another region. The breast region can be acquired by, for example, executing, by an image processing system (not shown), processing of detecting a body surface and a chest wall from a three-dimensional tomographic image of an object. Note that the object region may not be acquired from the data server 160. The object region may be acquired by performing image processing on a three-dimensional tomographic image in the image processing apparatus 100. In this step, the acquisition method is not limited to a specific one as long as information that defines an object region in the three-dimensional tomographic acquired in step S3000 can be acquired.

(Step S3020: Acquisition of Reference Point Position)

In step S3020, the reference point position acquisition unit 110 acquires a reference point position (papilla position in this embodiment) in the three-dimensional tomographic image acquired in step S3000. Various methods are conceivable as the reference point position acquisition method.

For example, a position input by the operator using an operation unit (not shown) may be acquired as the reference point position. For example, the operator inputs an instruction by operating the operation unit, and causes the image processing apparatus 100 to generate the two-dimensional tomographic image of an arbitrary slice from the three-dimensional tomographic image acquired in step S3000 and display it on the display unit 170. When the operator operates the operation unit to designate a position regarded as the papilla position on the two-dimensional tomographic image displayed on the display unit 170, the designated position in the three-dimensional tomographic image is specified as the papilla position based on the designated position and the position of the two-dimensional tomographic image in the three-dimensional tomographic image.

The image processing apparatus 100 may acquire the papilla position in the three-dimensional tomographic image by performing image analysis processing on the three-dimensional tomographic image acquired in step S3000.

When information indicating the papilla position in the three-dimensional tomographic image has already been registered in advance in the data server 160, the reference point position acquisition unit 110 suffices to acquire this information from the data server 160. In this manner, there are various methods as the reference point position acquisition method, and the acquisition method is not limited to a specific one in this embodiment.

(Step S3022: Acquisition of Region of Interest)

In step S3022, the region-of-interest acquisition unit 125 acquires information about "the region of interest in the object region" from the data server 160. When a region where the disease of an object exists has been known from a past examination, the region of interest is diagnosis information describing this region. For example, the region-of-interest acquisition unit 125 acquires information representing which of region A (cranial inside), region B (caudal inside), region C (cranial outside), region D (caudal outside), and region E (immediately below the papilla) is the region of interest.

Object regions are classified in advance into a plurality of regions (A to E in the above example) (for example, three-dimensional label images having values corresponding to the respective regions are generated). This classification processing can be performed in accordance with the definitions of the respective regions based on the papilla position and the barycentric position of the object region. Of the plurality of regions, a region corresponding to the information acquired in step S3022 is set as the region of interest.

Note that a region designated by the operator may be set as the region of interest. In the above example, one of regions A to E that is set as the region of interest may be switched at a proper timing, instead of setting only one of regions A to E as the region of interest.

Note that a region where the disease of an object exists may be unknown from a past examination, the presence/absence of a disease may be unknown, or information about "the region of interest in the object region" may not have been registered in the data server 160. In such a case, the processing in this step can be skipped.

(Step S3025: Acquisition of Initial Value of Reference Distance)

In step S3025, the reference distance acquisition unit 130 acquires and sets the initial value of the reference distance. The initial value of the reference distance may be a predetermined fixed value, or adaptively calculated in accordance with an object. For example, the reference distance acquisition unit 130 obtains the barycentric position of an object region defined by the information acquired in step S3010, and sets, as the initial value, the distance (when there are a plurality of three-dimensional tomographic images, a median or the like) from the reference point position to the barycentric position. When a reference distance to be applied to the object has already been registered in advance in the data server 160, the reference distance acquisition unit 130 acquires this reference distance as the initial value from the data server 160. In this way, various methods are conceivable as the method of setting the initial value of the reference distance, and this method is not limited to a specific one.

(Step S3030: Updating of Reference Distance)

In step S3030, every time a reference distance updating instruction is detected, the reference distance acquisition unit 130 updates the currently set reference distance in accordance with the updating instruction. That is, the image processing apparatus according to this embodiment further includes a unit (the reference distance acquisition unit 130) configured to change the radius (reference distance).

For example, every time it is detected that the operator has pressed a key assigned to an increase instruction on a keyboard serving as an operation unit or has rotated forward the wheel of a mouse serving as an operation unit, the reference distance acquisition unit 130 increases the reference distance. Also, every time it is detected that the operator has pressed a key assigned to a decrease instruction on the keyboard serving as an operation unit or has rotated backward the wheel of the mouse serving as an operation unit, the reference distance acquisition unit 130 decreases the reference distance. When the user directly inputs a reference distance by operating the operation unit, the reference distance acquisition unit 130 updates the current reference distance to the input reference distance.

When there are a plurality of three-dimensional tomographic images, it may be enabled to select a setting of giving (synchronizing) a common reference distance to the respective three-dimensional tomographic images, or a setting of individually giving reference distances to the respective three-dimensional tomographic images. In the latter case, after the user selects a three-dimensional tomographic image for which the reference distance is updated, the reference distance of the three-dimensional tomographic image is updated.

That is, the positional relationship between the reference position and the curved slice is common to a plurality of three-dimensional tomographic images. Also, the positional relationship between the reference position and the curved slice can be changed for each three-dimensional tomographic image.

(Step S3035: Setting of Field of View)

In step S3035, the field-of-view acquisition unit 135 obtains and sets a field of view used when generating a two-dimensional tomographic image from the three-dimensional tomographic image acquired in step S3000. In this embodiment, the field of view is defined by the direction (gazing direction) of the central axis of a cone (for example, a circular cone in the following description) having the vertex positioned at the reference point position, and the angle (viewing angle) at the vertex. The setting of the field of view is executed by, for example, the following processing.

First, the reference point position acquired in step S3020 is set as a center position, and a spherical surface whose radius is the reference distance finalized through the processing of step S3030 is set at the reference point position. Then, a partial spherical region (that is, an object region on the spherical surface) that belongs to the object region defined by the information acquired in step S3010 is obtained on this spherical surface. A circular cone that contains the partial spherical region and has a minimum angle at the vertex is obtained, and the field of view is defined by the obtained circular cone. When a region of interest has been designated in the processing of step S3022, a circular cone that contains this region of interest and has a minimum angle at the vertex is obtained, and the field of view is defined by the obtained circular cone. Accordingly, the field of view is set so that when no region of interest has been designated, an entire partial spherical region is displayed, and when a region of interest has been designated, only a region of interest is enlarged and displayed.

Note that updating of the field of view may be executed every time the reference distance is changed, or executed only when the processing of this step is executed for the first time or the operator designates updating of the field of view by operating the operation unit. Alternatively, a predetermined field of view may be used without calculating the field of view based on the object region. For example, when the relative positional relationship between an object and a reference point in a three-dimensional tomographic image is almost constant regardless of the case, a predetermined direction may be set as the gazing direction. For example, when the Y-axis is set in a direction from the ventral side to dorsal side of an object in the three-dimensional tomographic image of the breast, the Y-axis direction (direction from the papilla to the central portion of the breast) is defined as the gazing direction. As for the viewing angle, a predetermined value (for example, the solid angle $\pi$ [steradian] (equivalent to the semi-vertical angle of 60°)) may be given. When the data server 160 holds the value of a field of view to be applied to a three-dimensional tomographic image, the field-of-view acquisition unit 135 may acquire this value from the data server 160 and set it as the field of view.

Alternatively, the operator may be allowed to set the correction value of the field of view, and a value obtained by correcting, based on this correction value, the field of view obtained by the above processing may be defined as a field of view to be applied. For example, every time it is detected that the operator has pressed a key assigned to an increase instruction on a keyboard serving as an operation unit or has rotated forward the wheel of a mouse serving as an operation unit, the field-of-view acquisition unit 135 increases the correction value. Also, every time it is detected that the operator has pressed a key assigned to a decrease instruction on the keyboard serving as an operation unit or has rotated backward the wheel of the mouse serving as an operation unit, the field-of-view acquisition unit 135 decreases the correction value. When the user directly inputs a correction value by operating the operation unit, the field-of-view acquisition unit 135 updates the current correction value to the input correction value. The field-of-view acquisition unit 135 corrects the field of view by using the updated correction value. This similarly applies to a case where the gazing direction or another parameter is corrected.

When there are a plurality of three-dimensional tomographic images, it may be enabled to select a setting of simultaneously correcting (synchronizing) the fields of view and gazing directions of the respective three-dimensional tomographic images, or a setting of individually correcting them. In the latter case, after the user selects a three-dimensional tomographic image for which the field of view and the gazing direction are corrected, the field of view and the gazing direction are corrected.

(Step S3040: Generation of Tomogram)

In step S3040, the calculation unit 136 obtains, as the target region, a region (a partial spherical region or a region in the region of interest) belonging to the field of view in the partial spherical region. That is, the calculation unit 136 obtains, as the curved slice, a partial spherical region belonging to the object region in the three-dimensional tomographic image on the spherical surface based on a center on the reference position and the designated radius. The image generation unit 140 generates the two-dimensional tomographic image of the target region from the three-dimensional tomographic image acquired in step S3000. Processing for generating a two-dimensional tomographic image is executed by, for example, processing of obtaining the values of respective points in the target region in the three-dimensional tomographic image, and processing of projecting the values of the respective points to a plane to generate a two-dimensional tomographic image for display.

More specifically, the calculation unit 136 specifies a designated region in the object region in the three-dimensional tomographic image. The image generation unit 140 generates, from the three-dimensional tomographic image, the two-dimensional tomographic image of the region specified by the calculation unit 136.

The former processing can be implemented by, for example, acquiring voxel values equivalent to the positions of respective points in a target region by interpolation processing of the voxel value of a three-dimensional tomographic image. Alternatively, the maximum values of voxel values in a three-dimensional tomographic image in a predetermined range in the normal direction of a target region may be obtained for respective points in the target region (maximum value projection may be performed), and these values may be set as the values of the respective points. Note that the processing of obtaining the values of respective points in a target region may be based on any other method as long as it is based on the target region. These methods are desirably selectable in accordance with an instruction from the operator. When information about an object region and a region of interest (to be referred to as "object region or the like" altogether hereinafter) is obtained, and each point in the target region is not included in the object region or the like, the value of this point may be set to be 0. This has an effect capable of masking a region of no interest (for example, the greater pectoral muscle, the heart, or a region other than the region of interest), and efficiently observing the image. Note that it is desirable that the operator can select whether to execute masking.

The latter processing is implemented by applying a well-known projection of performing projection from a target region to a plane. For example, a well-known azimuthal equidistance projection or azimuthal equal-area projection is usable. Another projection is also usable. It is desirable that these projections are selectable in accordance with an instruction from the operator. Note that the image size of a two-dimensional tomographic image can be set to be a predetermined value regardless of the value of the field of view acquired in step S3035. For example, the image size of a two-dimensional tomographic image can be an image size adjusted to the size of the display region of the display unit 170. Hence, the enlarged/reduced display of a two-dimensional tomographic image corresponding to adjustment (decrease/increase) of the viewing angle in step S3035 is implemented.

Figure 4A:
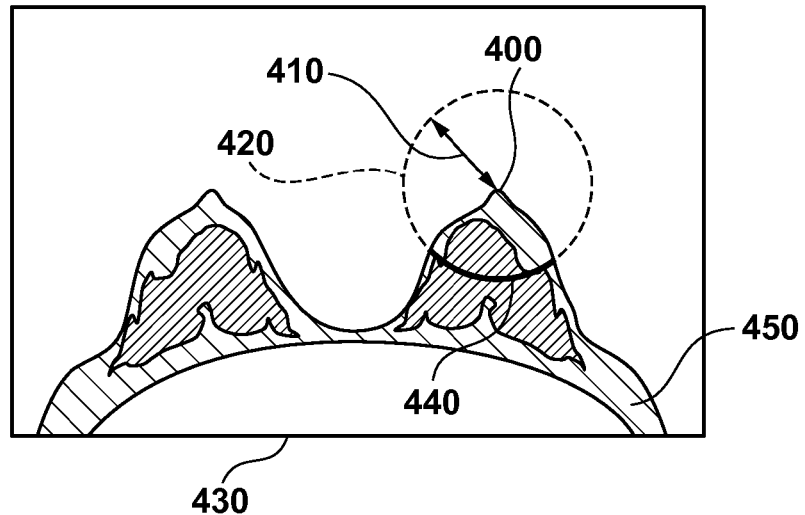
FIGS. 4A to 4C are views showing a two-dimensional tomographic image and the generation process.
Figure 4B:
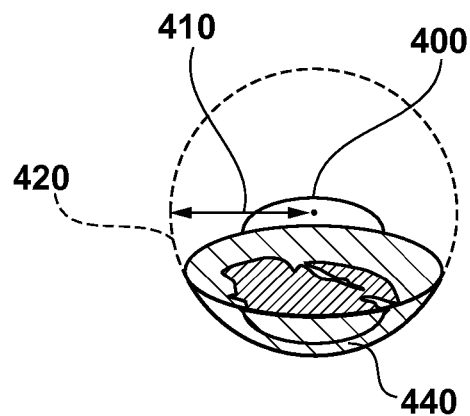
Figure 4C:
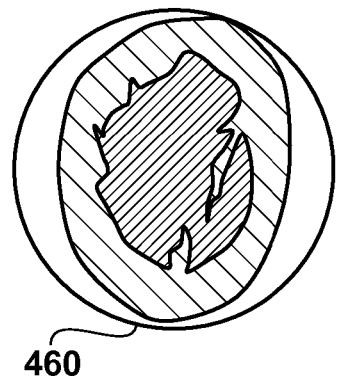

The image generation unit 140 sends the generated two-dimensional tomographic image to the display control unit 150. FIGS. 4A to 4C show a two-dimensional tomographic image generated from a three-dimensional tomographic image by the above-described processing, and the generation process.

FIG. 4A shows, on a given slice, the relationship between a three-dimensional tomographic image 430, a papilla position 400, a spherical surface 420 centered on the papilla position 400, a radius (reference distance) 410 of the spherical surface 420, and a target region (slice) 440.

FIG. 4B shows only the inside of the spherical surface 420. FIG. 4B three-dimensionally shows the spherical surface 420 centered on the papilla position 400 and having the reference distance 410 as the radius, and the slice 440 defined by the field of view. FIG. 4C shows a two-dimensional tomographic image 460 generated by clipping the slice 440 from the three-dimensional tomographic image 430.

Figure 5A:
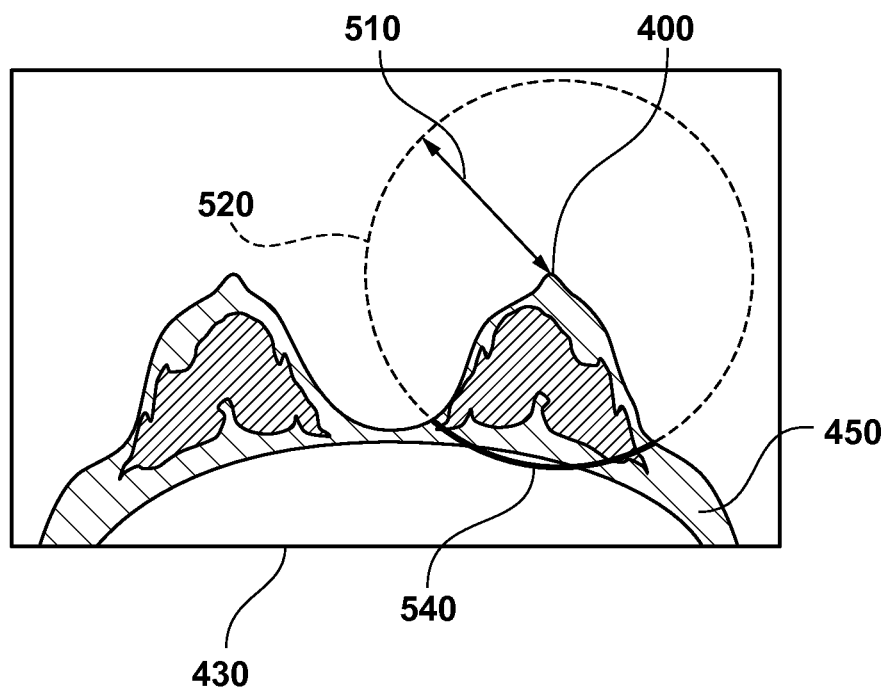
FIGS. 5A and 5B are views showing an example when a reference distance different from that in FIGS. 4A to 4C is set.
Figure 5B:
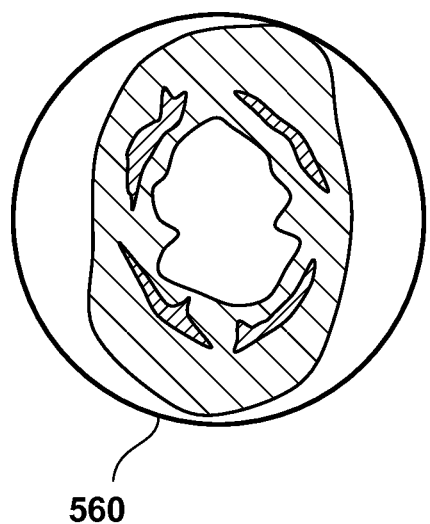

FIGS. 5A and 5B show an example when a reference distance different from that in FIGS. 4A to 4C is set. In this example, as shown in FIG. 5A, a slice 540 includes a region of no interest below the greater pectoral muscle surface because of a large reference distance 510 (a large spherical surface 520). In this case, an image in which the region of no interest is masked is generated as a two-dimensional tomographic image 560, as shown in FIG. 5B.

(Step S3045: Display of Tomogram)

In step S3045, the display control unit 150 controls the display unit 170 to display the two-dimensional tomographic image sent from the image generation unit 140. That is, the image processing apparatus according to this embodiment further includes a unit (the display unit 170) configured to display a two-dimensional tomographic image generated by the image generation unit 140. When the image acquisition unit 120 acquires a plurality of three-dimensional tomographic images and two-dimensional tomographic images are generated for the respective (or some) three-dimensional tomographic images up to this step, the display unit 170 may display the respective two-dimensional tomographic images. Alternatively, a two-dimensional tomographic image selected by the user using an operation unit may be displayed.

As described above, the two-dimensional tomographic image output destination is not limited to the display unit 170. For example, the snapshot of a two-dimensional tomographic image during display may be associated with a display parameter in accordance with a user instruction, and output to a memory inside or outside the image processing apparatus 100 or to the data server 160.

Together with the two-dimensional tomographic image obtained in step S3040, a normal two-dimensional tomographic image (for example, an axial tomogram, a sagittal tomogram, or a coronal tomogram: to be referred to as a planar tomogram hereinafter) obtained by clipping a three-dimensional tomographic image from a slice formed from a plane (to be referred to as a planar slice hereinafter) may be displayed. In this case, nodal lines between the spherical slice obtained in step S3040 and the planer slice are superposed and drawn on the planar tomogram. This makes it easy to grasp the positional relationship between the object and the spherical slice. It is also possible to acquire coordinates on a spherical tomogram during display that have been designated by an operation by the operator, and display a planar tomogram including these coordinates. In this case, a point of interest on the spherical tomogram can be quickly observed by a normal observation method such as 3-slice display.

(S3050: End Determination)

In step S3050, the control unit (not shown) of the image processing apparatus 100 determines whether the end condition of this processing has been satisfied. If the end condition has been satisfied, the process ends. If the end condition has not been satisfied, the process returns to step S3030. For example, when it is determined that the user has input an end instruction by operating the operation unit, it is determined that the end condition has been satisfied.

The image processing apparatus according to the present invention includes a calculation unit (the calculation unit 136) configured to obtain a curved slice from a three-dimensional tomographic image of an object based on a reference position in the three-dimensional tomographic image, and a generation unit (the image generation unit 140) configured to generate a two-dimensional tomographic image corresponding to the curved slice from the three-dimensional tomographic image.

When an object has a structural property in which the distance from a reference point to each point in the object does not greatly change, a two-dimensional tomographic image in which a region of interest is highly likely to exist can be reproducibly presented without cumbersome designation by the operator. Since a two-dimensional tomographic image that is highly likely to include a corresponding portion, out of a plurality of three-dimensional tomographic images, is displayed, the range of search by the operator can be limited. Therefore, the work load on the operator can be reduced, and the risk of wrong association can be reduced. Since the number of necessary operations is small, a search for a corresponding region can be supported without bothering the operator.

[Second Embodiment]

According to the second embodiment, the reference distance is calculated based on the position of a point of interest such as a lesion area designated in a three-dimensional tomographic image, and a two-dimensional tomographic image that is highly likely to include a point corresponding to the point of interest is generated from another three-dimensional tomographic image. A difference from the first embodiment will be mainly described below, and the remaining part is the same as that in the first embodiment, unless otherwise specified.

An example of the configuration of a system according to this embodiment will be described with reference to the block diagram of FIG. 6. Note that the same reference numerals in FIG. 6 denote the same functional units as those in FIG. 1, these functional units have been described in the first embodiment, and a description thereof will not be repeated.

As shown in FIG. 6, the system according to this embodiment is constituted by replacing the image processing apparatus 100 in the system according to the first embodiment shown in FIG. 1 with an image processing apparatus 600.

A point-of-interest position acquisition unit 615 acquires the position of a point of interest (point-of-interest position) in any one of a plurality of three-dimensional tomographic images acquired by an image acquisition unit 120.

Similarly to the region-of-interest acquisition unit 125, a region-of-interest acquisition unit 625 acquires information that defines a region of interest in the three-dimensional tomographic image acquired by the image acquisition unit 120. However, unlike the region-of-interest acquisition unit 125, the region-of-interest acquisition unit 625 acquires information that defines a region of interest based on the point-of-interest position.

Similarly to the reference distance acquisition unit 130, a reference distance acquisition unit 630 acquires a reference distance. However, unlike the reference distance acquisition unit 130, the reference distance acquisition unit 630 acquires a reference distance based on the reference point position and the point-of-interest position.

Figure 7:
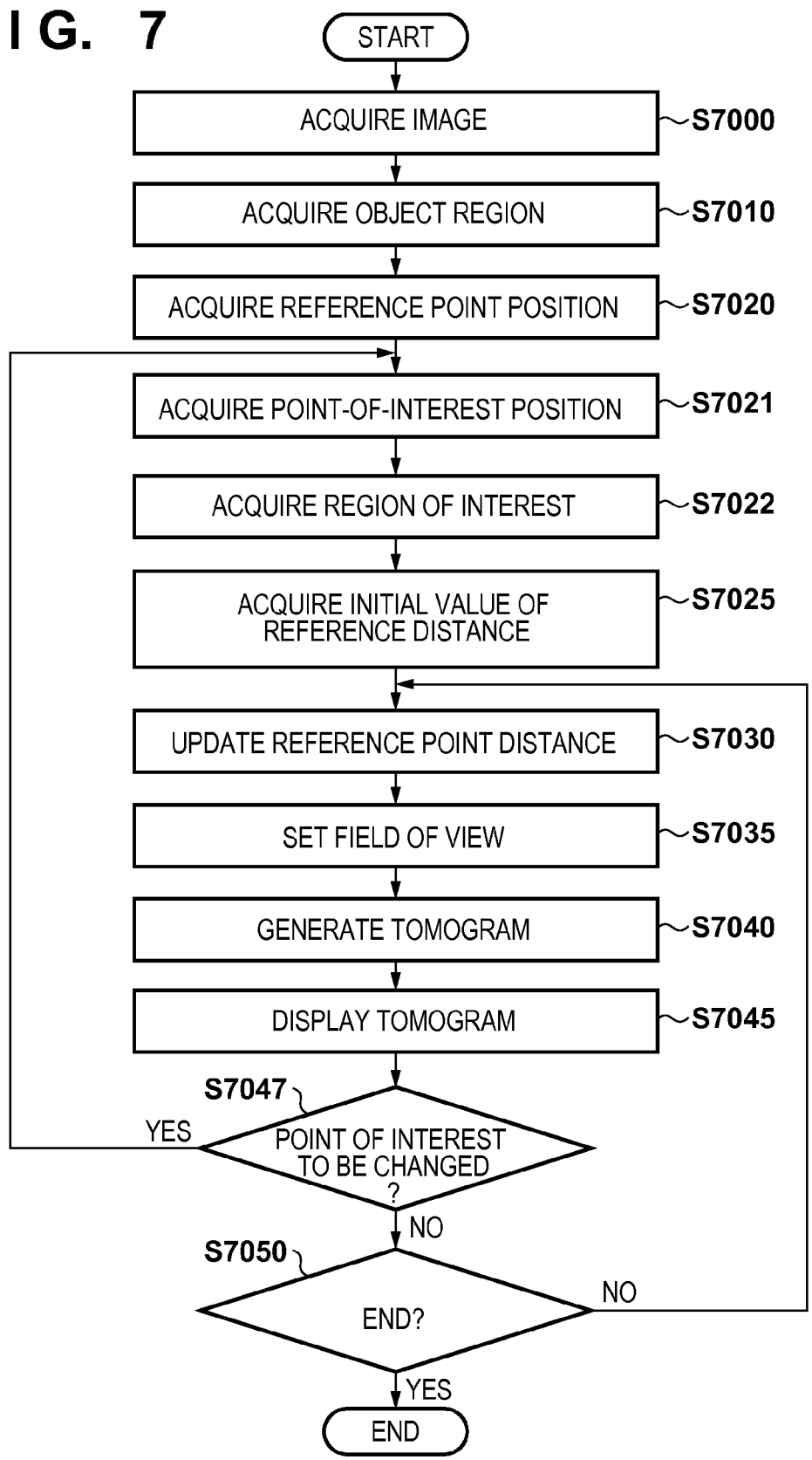
FIG. 7 is a flowchart showing processing to be performed by an image processing apparatus 600.

Next, processing to be performed by the image processing apparatus 600 will be explained with reference to the flowchart of FIG. 7. Note that steps S7000, S7010, S7020, S7030, S7035, S7040, S7045, and S7050 are the same as steps S3000, S3010, S3020, S3030, S3035, S3040, S3045, and S3050, respectively. Thus, a description of steps S7000, S7010, S7020, S7030, S7035, S7040, S7045, and S7050 will not be repeated.

(Step S7021: Acquisition of Point-of-Interest Position)

In step S7021, the point-of-interest position acquisition unit 615 acquires a point-of-interest position in any one of a plurality of three-dimensional tomographic images acquired by the image acquisition unit 120. Various methods are conceivable as the point-of-interest position acquisition method, similarly to the reference point position acquisition method in step S3020.

(Step S7022: Acquisition of Region of Interest)

In step S7022, the region-of-interest acquisition unit 625 acquires information about a region of interest in an object region based on the point-of-interest position acquired in step S7021. That is, a region (one of regions A to E in the example described in the first embodiment) to which the point-of-interest position belongs in the object region is determined, and the region (region including the point-of-interest position) to which the point-of-interest position belongs is set as a region of interest. It is desirable that whether to observe the entire object region or enlarge and observe only the region of interest can be properly switched by operating an operation unit by the operator.

(Step S7025: Acquisition of Initial Value of Reference Distance)

In step S7025, the reference distance acquisition unit 630 calculates, as the initial value of the reference distance, a distance to the point-of-interest position from the reference point position of the object in the three-dimensional tomographic image from which the point-of-interest position has been acquired.

(Step S7047: Determination of Change of Point of Interest)

In step S7047, the point-of-interest position acquisition unit 615 determines whether a point-of-interest change instruction has been detected. For example, when it is detected that the user has designated a new point of interest by using the operation unit, the point-of-interest position acquisition unit 615 determines that the point-of-interest change instruction has been detected. If it is determined that the point-of-interest change instruction has been detected, the process returns to step S7021. If the point-of-interest change instruction has not been detected, the process advances to step S7050.

FIGS. 8A to 8D show an example of output images generated by this processing. FIGS. 8A to 8D show an example when an MRI image 830 in a prone posture and an X-ray CT image 930 in a supine posture are acquired as three-dimensional tomographic images of an object, and the operator inputs a point of interest in the MRI image 830. The breast at the time of capturing these images is deformed owing to the difference in body posture, and this shape is different between images.

Figure 8A:
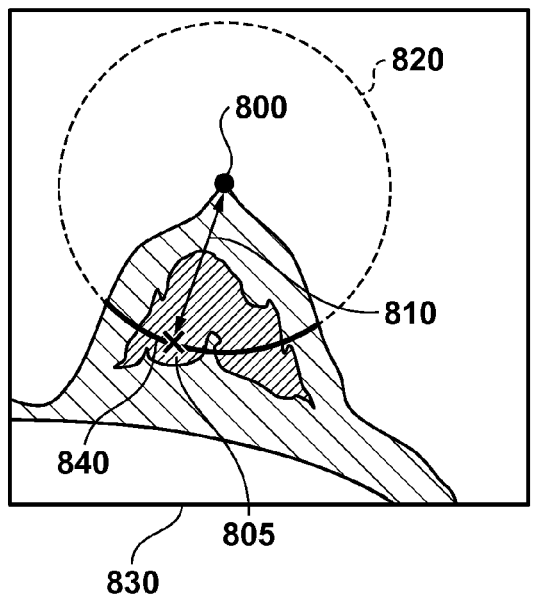
FIGS. 8A to 8D are views showing an example of output images.

FIG. 8A is a view showing a state in which one slice of the MRI image 830 is displayed. While the operator operates an operation unit and confirms the image of an arbitrary slice of the MRI image 830, he designates a point 805 of interest as a point of interest. The reference distance acquisition unit 630 calculates the distance between the point 805 of interest and an MRI reference point 800 as a reference distance 810.

Figure 8C:
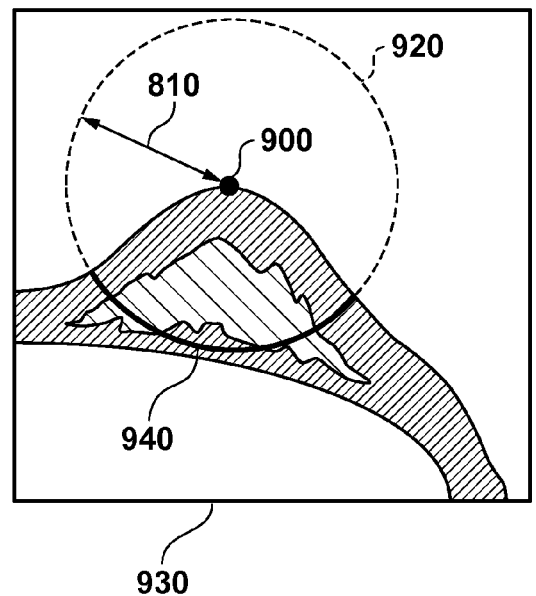
Figure 8B:
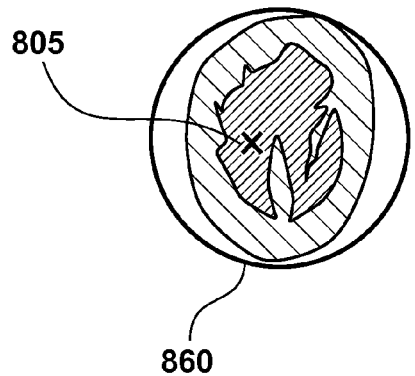

An image generation unit 140 clips a slice 840 determined by the reference distance 810 from the MRI image 830, thereby generating an MRI tomogram 860 including the point 805 of interest in the plane, as shown in FIG. 8B.

Figure 8D:
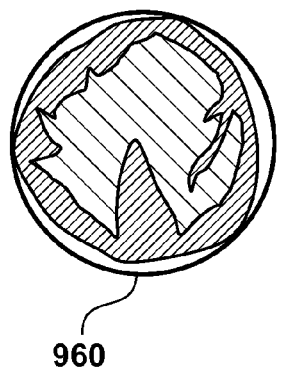

FIG. 8C shows the relationship between a reference point 900 in the X-ray CT image 930, the common reference distance 810, a spherical surface 920, and a slice 940. The image generation unit 140 clips the slice 940 determined by the reference distance 810 from the X-ray CT image 930, thereby generating a CT tomogram 960 as shown in FIG. 8D.

As described above, according to this embodiment, a tomogram always including a point of interest is generated from a three-dimensional tomographic image in which the point of interest is designated. Also, a tomogram that is highly likely to include the point of interest is generated from another three-dimensional tomographic image. When work of searching other three-dimensional tomographic images for a point corresponding to a point of interest designated in a given three-dimensional tomographic image is performed, tomograms that are highly likely to include the corresponding point can be easily generated from the respective three-dimensional tomographic images. By presenting these tomograms, a more effective point-of-interest search range can be presented to the operator. The labor of the operator can be reduced, and wrong association can be prevented. Even when the distance from a reference point to a point of interest is not completely maintained between images, the search can be easily performed by slightly correcting the reference distance for a target for which the hypothesis that a change of the distance is small is established.

(Modification 1)

Although a slice is generated from a spherical surface in the above embodiment, a slice need not be always generated from a perfect spherical surface, and another curved slice may be defined by a reference point and a reference distance. For example, a slice may be generated from an ellipsoidal surface centered on a reference point and having a reference distance as the major axis.

Also, a slice may be generated from a surface of an ellipsoidal shape similar to another sphere. A three-dimensional tomographic image may be cut into a shape whose radius increases from a position immediately below the papilla to the periphery. In this case, a tomogram (that is highly likely to include the same point) matching more an actual behavior of the object can be generated.

In short, it is only necessary to obtain (calculate), from a three-dimensional tomographic image of an object, a curved slice having a predetermined positional relationship with a reference position in the three-dimensional tomographic image, and generate a two-dimensional tomographic image in the curved slice from the three-dimensional tomographic image. That is, a calculation unit 136 obtains, as a curved slice, a spherical surface centered on the reference position and having a designated radius.

(Modification 2)

Although the above embodiment has explained a case where the object is the breast, the object is an arbitrary one other than the breast. That is, the object is arbitrary as long as the target tends to keep the distance from a predetermined reference point of the object to each point in the object. For example, the object may be an organ such as the brain or lung. For example, when the object is the brain, the reference point may be a characteristic point of the cranial bone (for example, a point where the sagittal suture and the lambdoid suture cross each other). When the object is the lung, the reference point may be the carina between the right and left main bronchi. When the object is the lung, for example, three-dimensional tomographic images at the time of inspiration and expiration can be compared. The object is not limited to an organ or a living body such as a human body, and may be an industrial product or the like such as a mechanical part.

[Third Embodiment]

The respective functional units constituting each of image processing apparatuses 100 and 600 shown in FIGS. 1 and 6 may be implemented by hardware, software, or a combination of hardware and software, as a matter of course.

Figure 2:
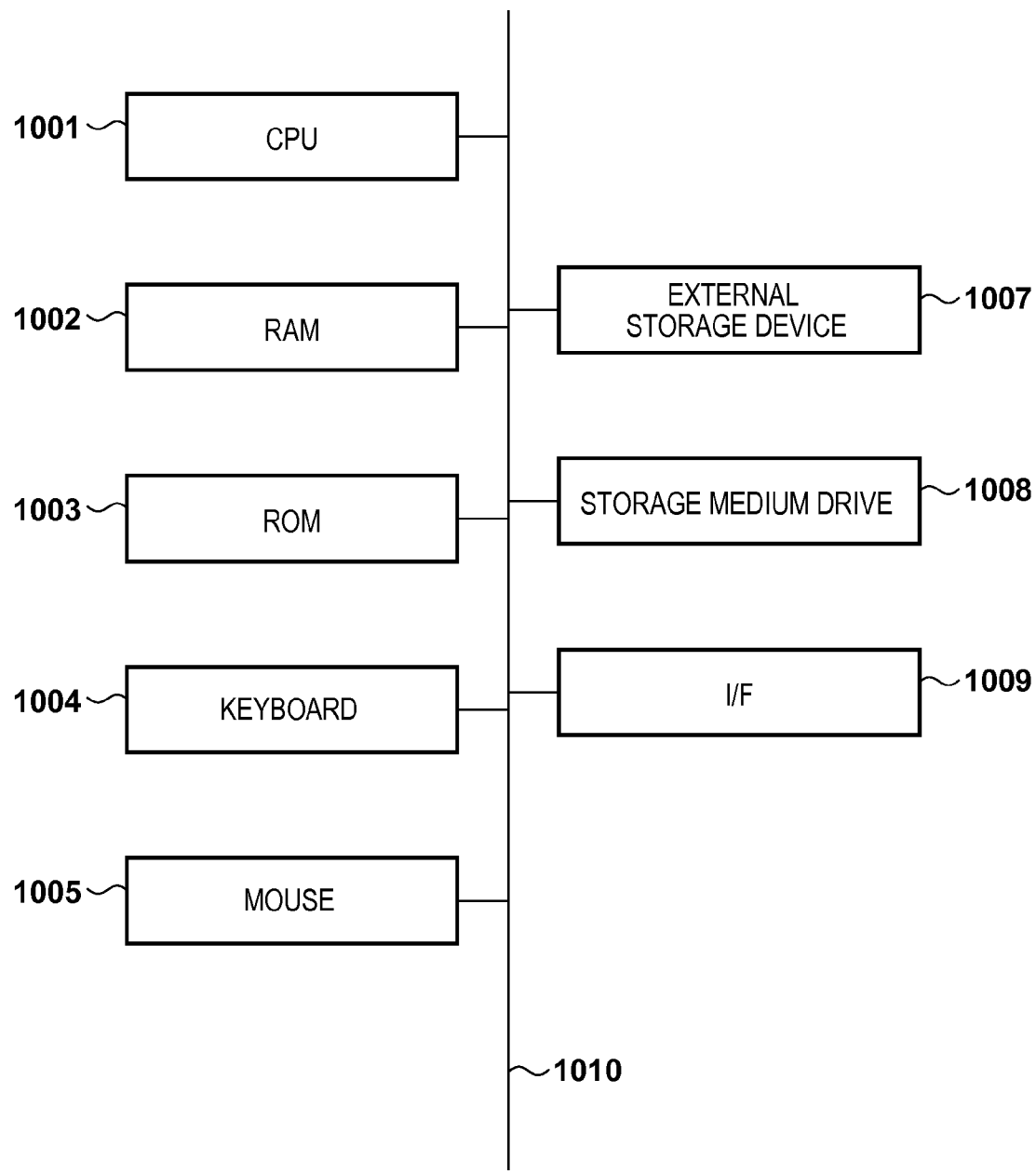
FIG. 2 is a block diagram showing an example of the configuration of a computer apparatus.

When the functional units constituting each of the image processing apparatuses 100 and 600 shown in FIGS. 1 and 6 are implemented by software, a computer apparatus having a configuration capable of executing this software can be applied to the image processing apparatus 100 or 600. An example of the configuration of such a computer apparatus will be explained with reference to the block diagram of FIG. 2.

A CPU 1001 executes processing by using computer programs and data stored in a RAM 1002 and a ROM 1003, thereby controlling the operation of the overall computer apparatus. In addition, the CPU 1001 executes each processing that is performed by the image processing apparatus 100 or 600 in the above description.

The RAM 1002 has an area for storing computer programs and data loaded from an external storage device 1007 and a storage medium drive 1008 and data received from the outside (for example, a data server 160) via an I/F (Interface) 1009. The RAM 1002 also has a work area used when the CPU 1001 executes various processes. In this fashion, the RAM 1002 can provide various areas, as needed. The ROM 1003 stores set data, boot programs, and the like for this apparatus.

A keyboard 1004 and a mouse 1005 are operated by an operator to input various instructions and data to the apparatus, and are used as, for example, the "operation units" in the above description.

The external storage device 1007 is a large-capacity information storage device typified by a hard disk drive device. The external storage device 1007 stores an OS (Operating System) and computer programs and data for causing the CPU 1001 to execute the processes that are performed by the image processing apparatus 100 or 600 in the above description. These computer programs include computer programs for causing the CPU 1001 to implement the functions of the functional units in each of the image processing apparatuses 100 and 600 shown in FIGS. 1 and 6. These data include those described above as known information, and various other parameters.

If necessary, the computer programs and data saved in the external storage device 1007 are loaded into the RAM 1002 and serve as processing targets by the CPU 1001 under the control of the CPU 1001.

The storage medium drive 1008 reads out a computer program and data recorded in a storage medium such as a CD-ROM or a DVD-ROM, and sends them to the RAM 1002 or the external storage device 1007.

The I/F 1009 is constituted by a digital input/output port such as an analog video port or IEEE1394, an Ethernet® port, or the like. The I/F 1009 allows connecting a display unit 170 and a data server 160 to this apparatus. The above-described building components are connected to each other via a bus 1010.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-026899, filed Feb. 14, 2014 which is hereby incorporated by reference herein in its entirety.

What is claimed is:

1. An image processing apparatus comprising:
one or more processors; and
at least one memory coupled to the one or more processors, the at least one memory having instructions stored thereon which, when executed by the one or more processors, cause the image processing apparatus to:
obtain a curved slice from a three-dimensional tomographic image of an object based on a reference position and a reference distance in the three-dimensional tomographic image; and
generate a two-dimensional tomographic image corresponding to the curved slice from the three-dimensional tomographic image,
wherein the curved slice is obtained having a predetermined positional relationship with the reference position in the three-dimensional tomographic image.

2. The apparatus according to claim 1, wherein the three-dimensional tomographic image is one of a plurality of three-dimensional tomographic images, and the instructions, when executed by the one or more processors, further cause the image processing apparatus to perform processes for each of the plurality of three-dimensional tomographic images.

3. The apparatus according to claim 2, wherein the predetermined positional relationship between the reference position and the curved slice is common to the plurality of three-dimensional tomographic images.

4. The apparatus according to claim 2, wherein the predetermined positional relationship between the reference position and the curved slice can be changed for each three-dimensional tomographic image.

5. The apparatus according to claim 1, wherein the instructions, when executed by the one or more processors, cause the image processing apparatus to obtain, as the curved slice, a spherical surface centered on the reference position.

6. The apparatus according to claim 1, wherein the instructions, when executed by the one or more processors, cause the image processing apparatus to obtain, as the curved slice, a partial spherical region belonging to a region of the object in the three-dimensional tomographic image on a spherical surface centered on the reference position.

7. The apparatus according to claim 1, wherein the instructions, when executed by the one or more processors, further cause the image processing apparatus to:
specify, from the curved slice, a designated region in a region of the object in the three-dimensional tomographic image, and
generate a two-dimensional tomographic image of the region specified from the three-dimensional tomographic image.

8. The apparatus according to claim 5, wherein the instructions, when executed by the one or more processors, further cause the image processing apparatus to change a radius of the spherical surface centered on the reference position.

9. The apparatus according to claim 1, wherein the instructions, when executed by the one or more processors, further cause the image processing apparatus to display the generated two-dimensional tomographic image.

10. The apparatus according to claim 1, wherein the instructions, when executed by the one or more processors, further cause the apparatus to:
acquire a position of a point of interest in the three-dimensional tomographic image, and
obtain the curved slice based on the reference distance corresponding to a distance from the reference position to the position of the point of interest.

11. The apparatus according to claim 10, wherein the instructions, when executed by the one or more processors, further cause the apparatus to:
obtain the reference distance in a first three-dimensional tomographic image, and
obtain the curved slice from a second three-dimensional tomographic image based on the reference distance in the first three-dimensional tomographic image.

12. The apparatus according to claim 1, wherein the three-dimensional tomographic image is one of a plurality of three-dimensional tomographic images, and the instructions, when executed by the one or more processors, further cause the apparatus to:
change the reference distance in each of the plurality of three-dimensional tomographic images in synchronization.

13. The apparatus according to claim 1, wherein the instructions, when executed by the one or more processors, cause the image processing apparatus to obtain, as the curved slice, an ellipsoidal surface centered on the reference position.

14. The apparatus according to claim 1, wherein the instructions, when executed by the one or more processors, cause the image processing apparatus to obtain the curved slice such that a plurality of distances from the reference position to a plurality of positions of the curved slice are different from each other.

15. An image processing method to be performed by an image processing apparatus, comprising:
obtaining a curved slice from a three-dimensional tomographic image of an object based on a reference position and a reference distance in the three-dimensional tomographic image; and
generating a two-dimensional tomographic image corresponding to the curved slice from the three-dimensional tomographic image,
wherein, in the obtaining, the curved slice having a predetermined positional relationship with the reference position in the three-dimensional tomographic image is obtained.

16. A non-transitory computer-readable storage medium storing a computer program for causing a computer to:
obtain a curved slice from a three-dimensional tomographic image of an object based on a reference position and a reference distance in the three-dimensional tomographic image; and
generate a two-dimensional tomographic image corresponding to the curved slice from the three-dimensional tomographic image,
wherein, in the obtaining, the curved slice having a predetermined positional relationship with the reference position in the three-dimensional tomographic image is obtained.

17. An image processing apparatus comprising:
one or more processors; and
at least one memory coupled to the one or more processors, the at least one memory having instructions stored thereon which, when executed by the one or more processors, cause the image processing apparatus to:
obtain a curved slice from a three-dimensional tomographic image of an object based on a reference position in the three-dimensional tomographic image; and
generate a two-dimensional tomographic image corresponding to the curved slice from the three-dimensional tomographic image,
wherein the curved slice is obtained having a predetermined positional relationship with the reference position in the three-dimensional tomographic image, and
wherein the object includes a breast, and the reference position corresponds to a position of a papilla.

* * * * *